(12) United States Patent
Livnat

(10) Patent No.: US 6,507,395 B1
(45) Date of Patent: Jan. 14, 2003

(54) ILLUMINATION HEAD

(75) Inventor: Yehiel Livnat, Irvine, CA (US)

(73) Assignee: Maxsys Technologies Corporation, Irvine, CA (US)

( * ) Notice: Subject to any disclaimer, the term of this patent is extended or adjusted under 35 U.S.C. 154(b) by 222 days.

(21) Appl. No.: 09/613,405

(22) Filed: Jul. 11, 2000

(51) Int. Cl.[7] .............................................. G01N 21/88
(52) U.S. Cl. .................................... 356/237.5; 356/394
(58) Field of Search .............................. 356/394, 237.1, 356/237.2, 237.3, 237.4, 237.5

(56) References Cited

U.S. PATENT DOCUMENTS

| | | | | |
|---|---|---|---|---|
| 4,421,410 A | * | 12/1983 | Karasaki | 356/394 |
| 4,677,531 A | * | 6/1987 | Szeles | 362/32 |
| 5,369,492 A | * | 11/1994 | Sugawara | 356/394 |
| 5,684,530 A | * | 11/1997 | White | 348/131 |

OTHER PUBLICATIONS

FOSTEC, Inc., FOSTEC Technical Specifications: PANELite Backlights, 1998.
FOSTEC, Inc., FOSTEC Technical Specifications: Darkfield Ringlight, 1996.
FOSTEC, Inc., FOSTEC Technical Specifications: Lightlines and Lenses, 1999.
FOSTEC, Inc., FOSTEC Technical Specifications: 1", 2", and 3" Lightlines, 1999.
FOSTEC, Inc., FOSTEC Technical Specifications: Continuous Lightlines, 1999.

* cited by examiner

*Primary Examiner*—Richard A. Rosenberger
(74) *Attorney, Agent, or Firm*—Stetina Brunda Garred & Brucker

(57) ABSTRACT

An illumination head for optical inspection of an upper surface of a printed circuit board. The illumination head comprises a backlight having an aperture formed therein for viewing the part and at least one lightline disposed adjacent to the backlight. The backlight and the lightline are operative to direct illumination on the part such that the illumination head may be disposed a prescribed distance above the part. Typically, the lightline provides illumination off-axis from the viewing axis of the part in order to increase contrast and decrease shadows on the part. In this respect, the illumination head may be positioned between 4 and 6 inches above the printed circuit board in order to permit reworking of the printed circuit board after a defect is found thereon.

20 Claims, 4 Drawing Sheets

ILLUMINATION HEAD

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention generally relates to an illumination head for printed circuit board verification and more particularly to an illumination head that may be disposed a prescribed distance above the printed circuit board in order to facilitate rework thereon.

In order to inspect printed circuit boards, it is desirable to illuminate the same with an illumination source. Typical illumination sources include rings of light and/or spotlights which direct light onto a top surface of the printed circuit board. In this regard, once the top surface of the printed circuit board is illuminated, the printed circuit board may be inspected through the use of a video camera and/or automated inspection technique.

It is desirable to illuminate the top surface of the printed circuit board such that shadows and/or glare which can impair inspection are eliminated. Therefore, in the prior art, the illumination head for an inspection station is disposed in close proximity to the top surface of the printed circuit board.

It is undesirable to have the illumination head disposed in close proximity to the top surface of the printed circuit board because reworking of a defective circuit board is difficult. Specifically, during inspection of the printed circuit board, the operator of the inspection station must determine where imperfections in the printed circuit board exist. Upon identifying such imperfections, the operator marks the imperfections and then removes the printed circuit board from the inspection station in order to rework the circuit board. Because the illumination head is positioned in close proximity to the top surface of the printed circuit board, the operator of the inspection station cannot effectuate repairs to the printed circuit board. Accordingly, the operator must mark and remove defective printed circuit boards in order to rework the same. Once the defect has been marked, rework on the printed circuit board is effectuated on another machine.

The present invention addresses the above-mentioned deficiencies in inspection stations by providing an illumination head for an inspection station that may be disposed 4 to 6 inches above the top surface of the printed circuit board and still generate a clear image of the inspected part. In this respect, reworking of the printed circuit board may be accomplished at the inspection station which includes the illumination head of the present invention. Accordingly, an operator using an inspection station having an illumination head of the present invention may find defects on the top surface of the printed circuit board and rework the same without removing the printed circuit board from the inspection station.

BRIEF SUMMARY OF THE INVENTION

An illumination head for an inspection and rework station. The illumination head has an optical axis and is operative to illuminate a part. The illumination head comprises a backlight having an aperture formed therein which is coaxially aligned with the optical axis of the illumination head. Further, the illumination head comprises at least one lightline disposed adjacent to the backlight. The backlight is operative to direct light onto the part along the optical axis and the lightline is operative to direct light onto the part at an angle incident to the optical axis. Accordingly, the illumination head may be disposed a prescribed distance above the part (i.e., typically four to six inches).

In accordance with the present invention, the aperture of the backlight may be circularly configured and the illumination head may further comprise an annular ringlight disposed between the backlight and the lightline. The ringlight is coaxially aligned with the aperture and operative to direct light onto the part along the optical axis. The lightline typically comprises two lightlines disposed on opposite sides of the illumination head. The illumination head may further comprise an iris coaxially aligned with the optical axis and configured to selectively regulate the level of illumination directed onto the part.

The illumination head constructed in accordance with the present invention may further include a viewing device coaxially aligned with the optical axis and operative to generate an image of the part through the aperture of the backlight. The viewing device may be a CCD camera.

In the preferred embodiment, the backlight is a translucent sheet configured to transmit light. The backlight is in optical communication through at least one optical fiber with a light source operative to illuminate the backlight. Similarly, the lightline may comprise a plurality of optical fibers disposed in substantially parallel relation to one another and operative to direct light upon the part at an angle incident to the optical axis.

In accordance with the present invention, there is provided a method of illuminating a part with an illumination head having an optical axis, a lightline, and a backlight. The method comprises illuminating the part with light directed at an angle incident to the optical axis with the lightline and illuminating the part with light directed along the optical axis with the backlight such that the illumination head is disposed a prescribed distance above the part. The method further may include coaxially aligning the aperture with the optical axis prior to illuminating the part.

In accordance with the present invention, the illumination head may further comprise an annular ringlight coaxially aligned with the aperture such that the method further comprises illuminating the part with light directed along the optical axis with the ring light. Additionally, the illumination head may further comprise an iris coaxially aligned with the aperture such that the method comprises controlling an amount of illumination from the backlight and the ringlight with the iris.

BRIEF DESCRIPTION OF THE DRAWINGS

These as well as other features of the present invention will become more apparent upon reference to the drawings wherein.

DETAILED DESCRIPTION OF THE INVENTION

Figure 1:
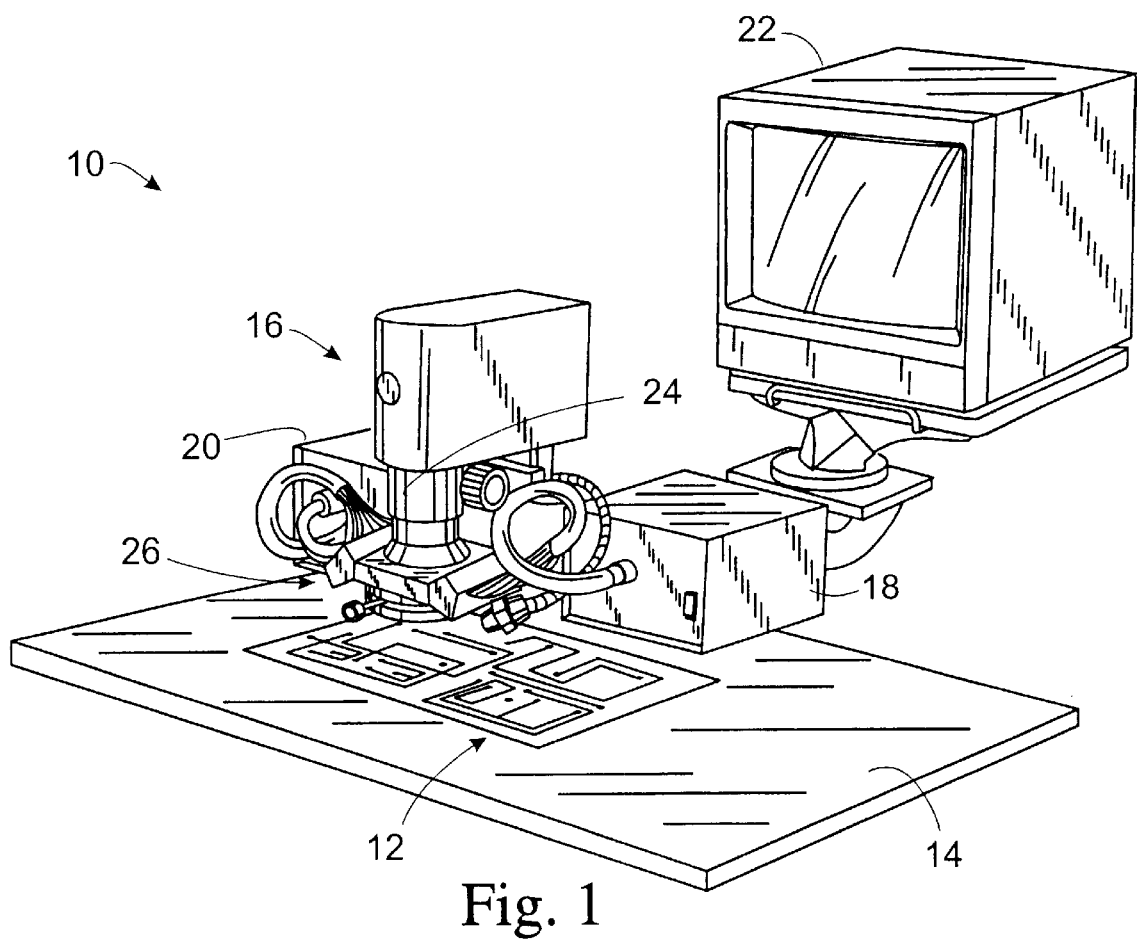
FIG. 1 is a perspective view of an illumination head constructed in accordance with a preferred embodiment of the present invention as used in conjunction with a verification and rework station.

Referring now to the drawings wherein the showings are for purposes of illustrating a preferred embodiment of the present invention only, and not for purposes of limiting the same, FIG. 1 perspectively illustrates a verification and rework station 10 used for inspection and reworking of a printed circuit board (PCB) 12. The verification and rework station 10 comprises a moveable x-y table 14 for supporting the printed circuit board 12. Disposed above the table 14 and printed circuit board 12 is a viewing unit 16 for directing illumination upon and imaging PCB 12. Disposed adjacent to the viewing unit 16 is a first light source 18 and a second light source 20. Both the first and second light sources 18, 20 provide illumination to the viewing unit 16, as will be further explained below. Furthermore, the verification and rework station 10 includes a monitor 22 in electrical communication with the viewing unit 16 for displaying an image of the PCB 12.

The verification and rework station 10 is used for the inspection of the PCB 12 after the manufacture thereof. In this respect, the viewing unit 16 is used to magnify the image of the PCB 12 in order to determine defects thereon. Illumination is directed upon the PCB12 by the viewing unit 16 and an image of the PCB 12 is created by the viewing unit 16. The image of the printed circuit board 12 is displayed on the monitor 22 in order to locate defects in the traces of the PCB 12. Once a defect in the traces of the printed circuit board 12 have been found, the operator of the verification and rework station 10 then effectuates repairs on the PCB 12. As previously mentioned, the PCB 12 is supported by table 14. In the preferred embodiment, table 14 of the verification and rework station 10 may be moveable along the x and y axis thereof in order to translate the PCB 12 under the viewing unit 16. The table 14 may include computer controlled motors (not shown) which translate the table 14 in a prescribed direction in order to facilitate viewing of the PCB 12 with the viewing unit 16.

Figure 5:
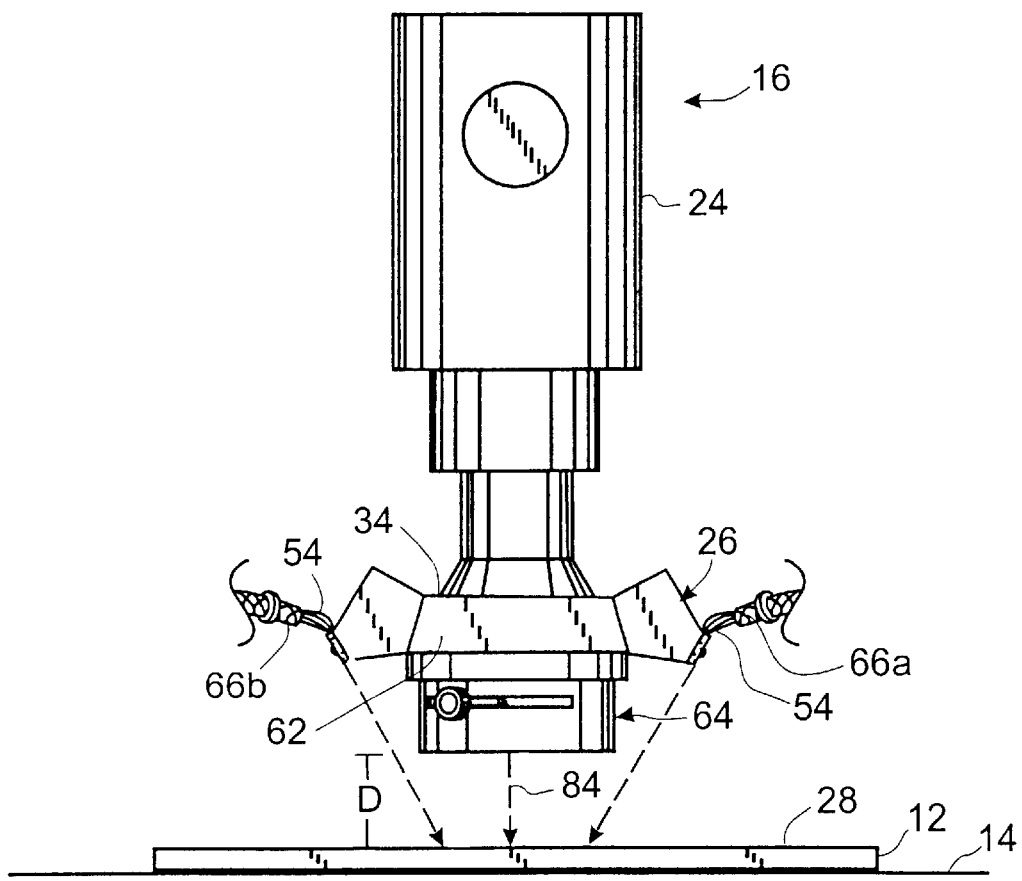
FIG. 5 is a side elevational view of the illumination head shown in FIG. 1 as used in conjunction with a viewing device.

Referring now to FIG. 5, the viewing unit 16 of the verification and rework station 10 comprises a camera 24 and an illumination head 26 constructed in accordance with the present invention. The illumination head 26 directs light onto an upper surface 28 of PCB 12. The illumination head 26 is operative to illuminate the upper surface 28 of the PCB 12 such that glare and shadows on the upper surface 28 thereof are reduced or eliminated. In this respect, the camera 24 images the tracings on the upper surface 28 of the PCB 12. Additionally, the illumination head 26 provides an adequate amount of light on the upper surface 28 such that the viewing unit 16 may be disposed above the upper surface 28 by a prescribed distance D, as seen in FIG. 5. In the preferred embodiment, distance D is approximately 4 to 6 inches such that an adequate working distance is provided for rework of the upper surface 28 of the PCB 12. By disposing the viewing unit 16 above the upper surface 28 of PCB 12 by about 4 to 6 inches, it is possible to rework the PCB 12 without removing the same from the table 14. Accordingly, time is saved during verification and rework of the printed circuit board 12 because the PCB 12 does not need to be removed from the verification and rework station 10 for correction of defects found thereon.

Figure 2:
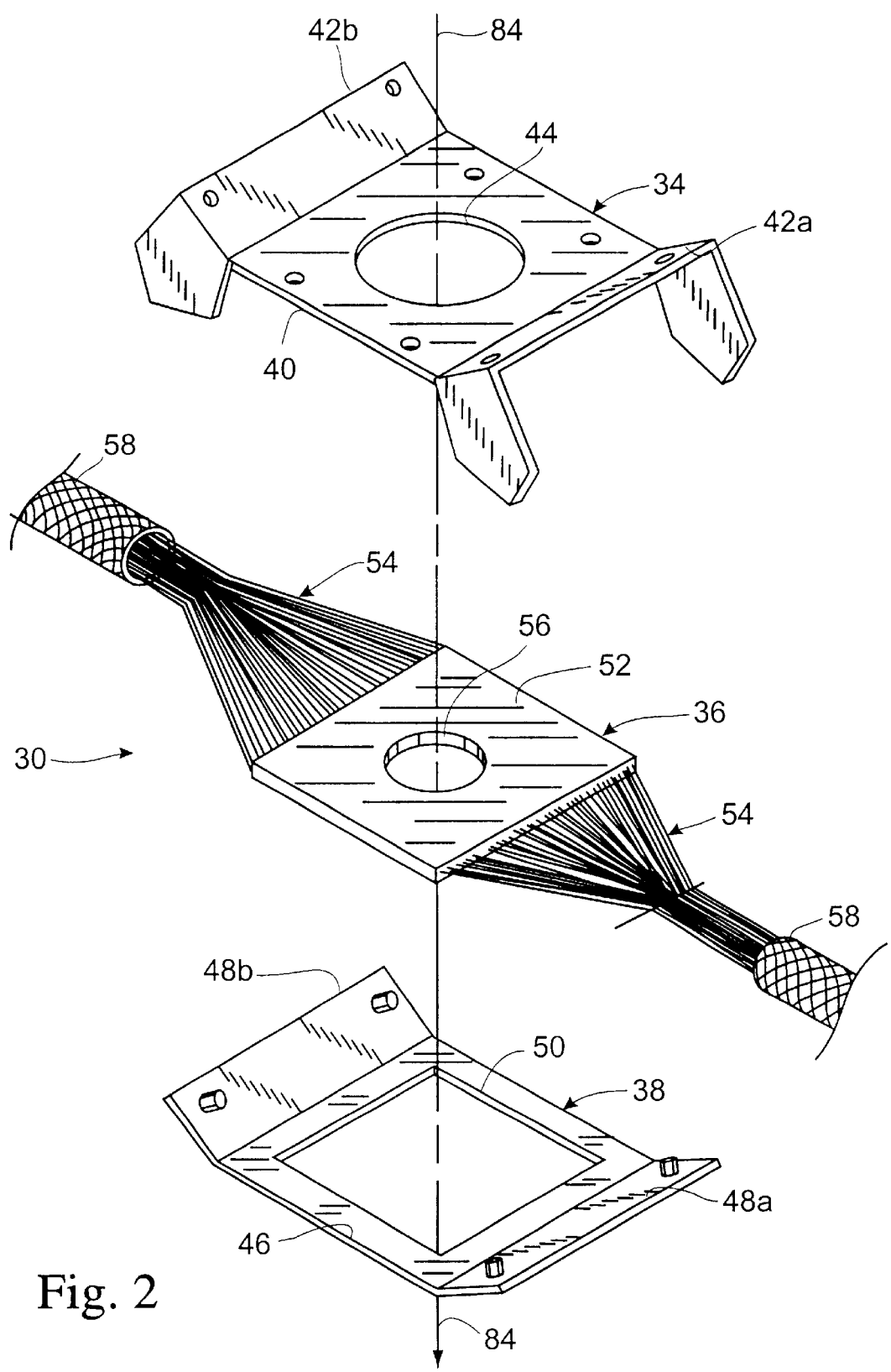
FIG. 2 is an exploded perspective view of an upper half of the illumination head shown in FIG. 1.
Figure 3:
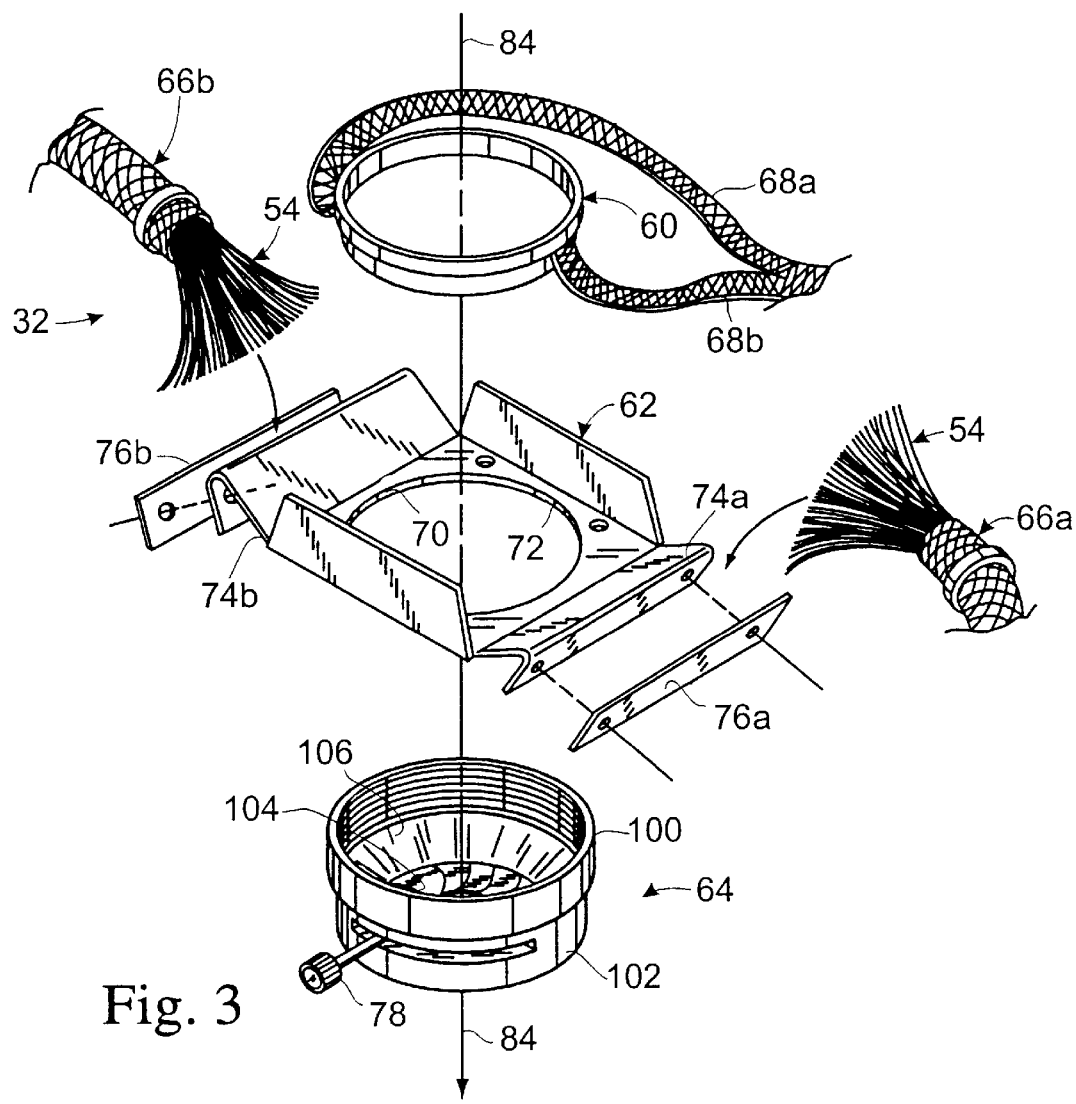
FIG. 3 is an exploded perspective view of a lower half of the illumination head shown in FIG. 1.

Referring to FIGS. 2 and 3, the illumination head 26 of the viewing unit 16 includes an upper portion 30 shown in FIG. 2 and a lower portion 32 shown in FIG. 3. It will be recognized that the upper portion 30 is attached to the lower portion 32 to form the complete illumination head 26. Referring to FIG. 2, the upper portion 30 of the illumination head 26 has a top support plate 34, a backlight 36, and a backlight support plate 38. The top support plate 34 is formed from a metallic material and comprises a generally planer center portion 40 and two flange portions 42a, 42b which extend along respective ones of an opposed pair of sides of the center portion 40. Each of the flange portions 42a, 42b is angled upwardly toward the camera 24 when the illumination head 26 is attached thereto. Furthermore, the top support plate 34 includes a circular aperture 44 disposed within the center portion 40. The backlight support plate 38 is formed from a metallic material and includes a generally planer center portion 46 and two flange portions 48a, 48b which extend along respective ones of an opposed pair of sides of the center portion 46. Similar to the top support plate 34, the flange portions 48a, 48b of the backlight support plate 38 are angled upwardly toward the camera 24. In this regard, the flange portions 48a, 48b of the backlight support plate are formed at the same angle as the flange portions 42a, 42b of the top support plate 34. Accordingly, when the illumination head 26 is assembled, the backlight support plate 38 will nest with the top support plate 34. As seen in FIG. 2, the backlight support plate 38 includes a generally square cutout 50 disposed in the center portion 46 thereof. The cutout 50 is sized approximately equal to the backlight 36, as will be further explained below.

Sandwiched between the top support plate 34 and the backlight support plate 38 is the backlight 36, as seen in FIG. 2. The backlight 36 is a generally translucent planar sheet 52 of plastic material in optical communication with a series of optical fibers 54. The backlight 36 includes a circular aperture 56 formed in the sheet 52. The optical fibers 54 are enclosed within a sheath 58. Each of the optical fibers 54 may be in optical communication with either the first light source 18 and/or the second light source 20 such that light will be transmitted via the optical fibers 54 to the translucent sheet 52. In this regard, the translucent sheet 52 will illuminate the area below the cutout 50 of the backlight support plate 38. Accordingly, the cutout 50 must be sized approximately equal to the size of the sheet 52 in order to transmit the maximum amount of light through the cutout 50.

The backlight 36 is a flexible plastic panel which will emit light from the lower surface thereof. In this respect, the flexible panel comprises a series of layers in optical communication with the optical fibers 54 such that the layers emit light. Such type of panel is manufactured by Lumitex, Inc., of Stronsville, Ohio.

As mentioned above, the backlight 36 is disposed between the top support plate 34 and the backlight support plate 38. Accordingly, the flange portions 42a, 42b of the top support plate 34, as well as the flange portions 48a, 48b of the backlight support plate 38, support and guide the optical fibers 54. In this respect, when the sheet 52 is sandwiched between the center portion 46 of the backlight support plate 38 and the center portion 40 of the top support plate 34, the optical fibers 54 extending from both sides of the sheet 52 will be positioned over the flange portions 48a, 48b of the backlight support plate 38.

Referring to FIG. 3, the lower portion 32 of the illumination head 26 may include a dark field ringlight 60, a metallic ring mount 62, an iris assembly 64, and first and second lightlines 66a, 66b. The ringlight 60 is a circular, translucent ring in optical communication with optical conduits 68a and 68b. Each of the optical conduits 68a, 68b comprise a plurality of optical fibers operative to transmit light to the circular ringlight 60. In this respect, the optical fibers are in direct optical communication with the direct light source 18 and/or 20 and collectively emit generally spiral lighting pattern within the interior of the ringlight 60.

The ringlight 60 is mounted to the metallic ring mount 62. In this respect, the ring mount 62 includes a generally planar center section 70 with a circular aperture 72 formed therein. The radius of the circular aperture 72 is approximately equal to the radius of the ringlight 60 such that the ringlight 60 may be mounted to the center section 70 of the ring mount 62. Accordingly, when the ringlight 60 is attached to the center section 70, light transmitted by the ringlight 60 will be directed parallel to an optical axis of the illumination head 26, as will be further explained below.

As seen in FIG. 3, the ring mount 62 further includes angled lightline mounting sections 74a and 74b. Each of the lightline mounting sections 74a, 74b are angled approximately equal to the flange portions 48a, 48b of the backlight support plate 38. In this respect, when the illumination head 26 is fully assembled, the lightline mounting sections 74a, 74b will nest with respective flange portions 48a, 48b of the backlight support plate 38. Attached to lightline mounting section 74a is lightline 66a comprising a plurality of optical fibers 54. The lightline 66a is attached to the lightline mounting section 74a by sandwiching the optical fibers 54 between the lightline mounting section 74a and a lightline mounting plate 76a. The optical fibers 54 of the lightline 66a are captured between the lightline mounting section 74a and the lightline mounting plate 76a in a fan-like manner such that the optical fibers 54 direct light downwardly at an angle from the ring mount 62. Similarly, lightline 66b is attached to lightline mounting section 74b through the use of lightline mounting plate 76b. The lightlines 66a, 66b direct light onto a top surface 28 of the PCB 12 at an angle in order to remove shadows. In this respect, lightline 66a projects light from one side of the illumination head 26, while lightline 66b projects light from an opposite side of the illumination head 26. As seen in FIG. 5, the lightlines 66a, 66b illuminate the top surface 28 of PCB 12 at an angle not normal to the top surface 28. The optical filters 54 of the lightlines 66a, 66b are in optical communication with the first and/or second light sources 18, 20.

Figure 4:
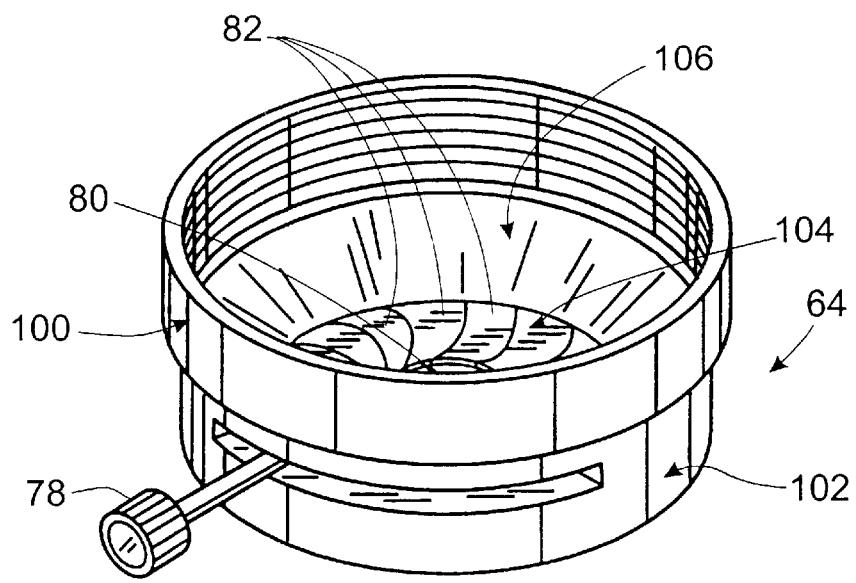
FIG. 4 is a perspective view of an iris used with the illumination head shown in FIG. 1.

Referring to FIG. 3, the iris assembly 64 of the illumination head 26 is attached to a lower surface of the center section 70 of ring mount 62. The iris assembly 64 includes a generally cylindrical upper member 100 having threads disposed on an inner surface thereof. Further, the iris assembly 64 includes a generally cylindrical lower member 102 having an iris 104 disposed therein. As seen in FIG. 4, the iris 104 is disposed within the center of the lower member 102. The lower member 102 defines a generally cone shaped inner surface 106 covered with a reflective material. The inner surface 106 transitions the upper member 100 and the iris 104. The inner surface 106 is reflective such that light striking the generally cone shaped inner surface 106 will be reflected. The lower member 102 further includes a control lever 78 operative to control the size of an aperture 80 formed by the iris 104. In this respect, the iris 104 is a conventional iris comprising multiple overlapping leaves 82 which, when it adjusted by lever 78, can increase or decrease the size of the aperture 80. The outer surface of the lower member 102 comprises a series of threads (not shown) which are engageable to the threads disposed within the interior surface of the upper member 100. In this respect, the lower member 102 can be rotated to adjust the height of the iris 104. More specifically, by rotating the lower member 102, the height of the iris 104 from the PCB 12 can be adjusted for the desired shadow field of illumination. As will be explained below, by adjusting the size of the aperture 80 with lever 78 and the distance of the iris 104 and inner surface 106 of lower member 102 from ring light 60, it is possible to control the amount of light emitted onto the top surface of the PCB 12 to create a desired shadow field of illumination.

Referring to FIGS. 2 and 3, the illumination head 26 defines an optical axis 84. Specifically, the optical axis 84 provides a line of sight for the camera 24 to view the PCB 12. The optical axis 84 is defined by the circular aperture 44 of the top support plate 34, the circular aperture 56 of the backlight 36, the cutout 50 of the backlight support plate 38, the ringlight 60, the circular aperture 72 of the ring mount 62, and the aperture 80 of the iris 64. As is evident, the optical axis 84 provides a clear line of sight from the camera 24 to the top surface 28 of the PCB 12. Additionally, as well as providing a line of sight, the optical axis 84 provides an illumination path for light to travel to the PCB 12. Specifically, referring to FIG. 2, light emitted from the backlight 36 will travel to the PCB 12 via cutout 50, ringlight 60, aperture 72 of ring mount 62, and aperture 80 of iris 64. Similarly, light transmitted by ringlight 60 will travel to PCB 12 via aperture 72 of ring mount 62 and aperture 80 of iris 104. Therefore, the backlight 36, as well as the ringlight 60, provide illumination normal to the top surface 28 of PCB 12. As mentioned above, lightline 66a and 66b provide illumination off-axis from optical axis 84 to thereby increase contrast and eliminate shadows.

Because the iris 104 is disposed within optical path 84, the iris 104 is operative to control the amount of illumination emitted from the ringlight 60 and backlight 36. Accordingly, iris 104 will divert the light from the ringlight 60 and backlight 36, as well as provide a variable field of view. The iris 104 is a passive component operative to control the amount of illumination directed upon the PCB 12 and will not degrade over time like active components such as polarizing filters. Additionally, the reflective inner surface 106 of the lower member 102 reflects light from the ring light 60 and back light 36. By adjusting the height of the iris 104 and inner surface 106, it is possible to adjust the light projected upon the top of the PCB 12. It will be recognized that height of the lower member 102 is adjusted by screwing the lower member 102 up or down within the upper member 100. The iris 104 and the height of the lower member 102 above the top surface of the PCB 12 functions to control the intensity of the light from the ring light 60 and back light 36 on the top surface of the PCB 12 such that a desired shadow field illumination is created for illuminating the upper surface 28 of PCB 12.

As previously mentioned, the camera 24 views the upper surface 28 of the PCB 12 via the optical axis 84. The ringlight 60, backlight 36, and lightlines 66a, 66b provide shadow field illumination as opposed to bright field illumination on the upper surface 28 of the PCB 12. Accordingly, the upper surface 28 is illuminated without shadow or glare for proper viewing by the camera 24. As seen in FIG. 5, the camera 24 is attached to the top support plate 34 such that the camera 24 views the upper surface 28 of the PCB 12 via the optical axis 84. The backlight 36, along with ringlight 60 (directing light through iris assembly 64) provide a shadow field effect without the use of a polarizing filter. As previously mentioned, since polarizing filters degrade over time, their use is disadvantaged. Accordingly, the illumination head 26 of the present invention provides a method whereby a shadow field effect is achieved without the use of a polarizing filter.

The illumination head 26 of the present invention is further constructed so as to be modular. In this respect, the use of the ringlight 60 and lower member 102 is optional. Furthermore, the illumination head 26 of the present invention provides a low profile thereby decreasing the size of the viewing unit 16. Additionally, the use of lightlines 66a, 66b, in conjunction with the backlight 36, increases the intensity of light on the upper surface 28 of the PCB 12 such that the viewing unit 16 may be located 4 to 6 inches above the PCB 12.

Additional modifications and improvements of the present invention such as including other types of illumination devices may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. An illumination head having an optical axis and operative to illuminate a part, the illumination head comprising:
    a backlight having an aperture formed therein which is coaxially aligned with the optical axis of the illumination head; and
    at least one lightline disposed adjacent to the backlight;
        wherein the backlight is operative to direct light onto the part along the optical axis and the lightline is operative to direct light onto the part at an angle incident to the optical axis such that the illumination head may be disposed a prescribed distance above the part.

2. The illumination head of claim 1 wherein the prescribed distance above the part is in the range of from about four to six inches.

3. The illumination head of claim 1 wherein:
    the aperture is circularly configured; and
    an annular ringlight is disposed between the backlight and the lightline, the ringlight being coaxially aligned with the aperture and operative to direct light onto the part along the optical axis.

4. The illumination head of claim 1 wherein the at least one lightline comprises two lightlines.

5. The illumination head of claim 1 further comprising an iris coaxially aligned with the optical axis.

6. The illumination head of claim 5 wherein the iris is configured to selectively regulate the level of illumination directed onto the part.

7. The illumination head of claim 1 further comprising a viewing device coaxially aligned with the optical axis and operative to generate an image of the part through the aperture.

8. The illumination head of claim 7 wherein the viewing device is a CCD camera.

9. The illumination head of claim 1 wherein the backlight comprises a translucent sheet configured to transmit light.

10. The illumination head of claim 9 wherein the backlight is in optical communication with a light source operative to illuminate the backlight.

11. The illumination head of claim 10 wherein the illumination head includes at least one optical fiber in optical communication with the light source and the backlight.

12. The illumination head of claim 1 wherein the at least one lightline comprises a plurality of optical fibers disposed in substantially parallel relation to one another and operative to direct light upon the part at an angle incident to the optical axis.

13. A method of illuminating a part with an illumination head having an optical axis, a lightline and a backlight, the method comprising the steps:
    a) illuminating the part with light directed at an angle incident to the optical axis with the lightline; and
    b) illuminating the part with light directed along the optical axis with the backlight such that the illumination head is disposed a prescribed distance above the part.

14. The method of claim 13 wherein the backlight includes an aperture and step (b) comprises coaxially aligning the aperture with the optical axis prior to illuminating the part.

15. The method of claim 14 wherein the aperture of the backlight is generally circular and the illumination head further comprises an annular ringlight coaxially aligned with the aperture, the method further comprising the step:
    c) illuminating the part with light directed along the optical axis with the ringlight.

16. The method of claim 15 wherein the illumination head further comprises an iris coaxially aligned with the aperture, the method further comprising the step:
    d) controlling an amount of illumination from the backlight and the ringlight with the iris.

17. The method of claim 16 further comprising the step:
    e) viewing the part with a viewing device coaxially aligned with the optical path.

18. The method of claim 17 wherein the viewing device is a CCD camera.

19. The method of claim 13 wherein the backlight is a translucent sheet and step (b) comprises illuminating the part with the backlight by illuminating the translucent sheet.

20. The method of claim 13 wherein the part is illuminated such that the illumination head is disposed about four to six inches above the part.

* * * * *